United States Patent
Bode et al.

(10) Patent No.: US 10,532,040 B2
(45) Date of Patent: Jan. 14, 2020

(54) METHODS OF TREATING CANCER WITH HERBACETIN

(71) Applicant: REGENTS OF THE UNIVERSITY OF MINNESOTA, Minneapolis, MN (US)

(72) Inventors: Ann M. Bode, Minneapolis, MN (US); Young-Yeon Cho, Minneapolis, MN (US); Zigang Dong, Minneapolis, MN (US); Dong Joon Kim, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 971 days.

(21) Appl. No.: 14/357,860

(22) PCT Filed: Nov. 19, 2012

(86) PCT No.: PCT/US2012/065898
§ 371 (c)(1),
(2) Date: May 13, 2014

(87) PCT Pub. No.: WO2013/075120
PCT Pub. Date: May 23, 2013

(65) Prior Publication Data
US 2014/0303244 A1    Oct. 9, 2014

Related U.S. Application Data

(60) Provisional application No. 61/565,320, filed on Nov. 30, 2011, provisional application No. 61/561,436, filed on Nov. 18, 2011.

(51) Int. Cl.
*A61K 31/35* (2006.01)
*A61K 31/353* (2006.01)
*A61K 31/352* (2006.01)

(52) U.S. Cl.
CPC .......... *A61K 31/353* (2013.01); *A61K 31/352* (2013.01)

(58) Field of Classification Search
CPC ........................... A61K 31/353; A61K 31/352
(Continued)

(56) References Cited

U.S. PATENT DOCUMENTS 4,559,157 A    12/1985 Smith
4,774,229 A     9/1988 Jordan
(Continued)

FOREIGN PATENT DOCUMENTS

EP    2 130 544 A2 * 12/2006 ............. A61K 36/00
WO    WO 87/06833    * 11/1987

OTHER PUBLICATIONS

Bhatia, et al., Nutrition and Cancer, 39(2), 292-299, 2001.*
(Continued)

*Primary Examiner* — Shengjun Wang
(74) *Attorney, Agent, or Firm* — Viksnins Harris Padys Malen LLP

(57) ABSTRACT

The invention provides methods, uses and compounds for treating cancers. For example, certain embodiments provide a method for treating cancer in a mammal comprising administering to the mammal an effective amount of 3,5,7,8,4'-Pentahydroxyflavone, or a pharmaceutically acceptable salt thereof. Certain other embodiments of the invention provide methods for inactivating ornithine decarboxylase (ODC) in a cell comprising contacting the cell in vitro or in vivo with an effective amount of 3,5,7,8,4'-Pentahydroxyflavone, or a pharmaceutically acceptable salt thereof. The invention also provides a dermal product comprising 3,5,7,8,4'-Pentahydroxyflavone, or a pharmaceutically acceptable salt thereof, wherein the product prophylactically or therapeutically treats sunburn or other sun exposure and/or skin cancer in a mammal.

(Continued)

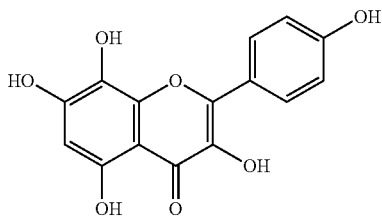

9 Claims, 15 Drawing Sheets

(58) Field of Classification Search
USPC .......................................................... 514/456
See application file for complete search history.

(56) References Cited

U.S. PATENT DOCUMENTS

| | | | |
|---|---|---|---|
| 7,803,902 B2 * | 9/2010 | Amin ................... | C07K 14/811 530/324 |
| 2002/0006913 A1 | 1/2002 | Von Borstel et al. | |
| 2006/0234948 A1 | 10/2006 | Empie et al. | |
| 2010/0099755 A1 | 4/2010 | Cushman et al. | |

OTHER PUBLICATIONS

Chen et al., Chemistry and Physics of Lipids, 79, (1996), pp. 157-163.*
Brown and Jacoby, Mini-reviews in Medicinal Chemistry, 2006, 6, 12117-1229.*
CDC Skin Cancer Online Article http://www.cdc.gov/cancer/skin/basic_info/prevention.htm.*
Zhao, Hongyu, Drug Discovery Today, vol. 12, Nos. 3/4, Feb. 2007, pp. 149-155.*
Auvinen et al., "Ornithine decarboxylase activity is critical for cell transformation", *Nature 360*, 355-358 (1992).
Bailey et al., "A randomized, double-blind, placebo-controlled phase 3 skin cancer prevention study of {alpha}-difluoromethylornithine in subjects with previous history of skin cancer", *Cancer Prev Res (Philia) 3*, 35-47 (2010).
Berman et al., "The Protein Data Bank", *Nucleic Acids Res 28*, 235-242 (2000).
Boyd et al., "Identification of target genes of oncogenic transcription factors", *Proc Soc Exp Biol Med 222*, 9-28 (1999).
Casero et al., "Targeting polyamine metabolism and function in cancer and other hyperproliferative diseases", *Nat. Rev Drug Discov 6*, 373-390 (2007).
Dong et al., "Mitochondrial targeting of α-tocopheryl succinate enhances its pro-apoptotic efficacy: A new paradigm for effective cancer therapy", *Free Radical Biology & Medicine 50*, 1546-1555 (2011).
Franski et al., "Electrospray mass spectrometric decomposition of some glucuronic acid-containing flavonoid diglycosies", *Phytochem Anal 14*(3), 170-175 (2003).
Friesner et al., "Glide: a new approach for rapid, accurate docking and scoring", *Journal of Medicinal Chemistry 47*, 1739-1749 (2004).
Ganju et al., "Phase I study of combined alpha interferon, aopha difluoromethylornithine (DFMO), and doxorubicin in advanced malignancy", *Invest New Drugs 12*, 25-27 (1994).
Gedara et al., "New erythroxane-type diterpenoids from Fagonia boveana (Hadidi) Hadidi & Graf.", *Z Naturforsch C 58* (1-2), 23-32 (2003).
Gerner et al., "Polyamines and cancer: old molecules, new understanding", *Nat Rev Cancer 4*, 781-792 (2004).
Grougnet et al., "Seco-Cycloartane triterpenes from Gardenia aubryi", *J. Nat. Prod. 69* (12), 1711-1714 (2006).

Holtta et al., "The mechanisms of ornithine decarboxylase deregulation in c-Ha-ras oncogene-transformed NIH 3T3 cells", *J Biol Chem 263*, 4500-4507 (1988).
Horn et al., "Phase I-II clinical trial with alpha-difluoromethylornithine—an inhibitor of polyamine biosynthesis", *Eur J Cancer Clin Oncol 23*, 1103-1107 (1987).
Huang et al., "Systematic and integrative analysis of large gene lists using David bioinformatics resources", *Nat Protoc 4*, 44-57 (2009).
Hyuga et al., "Herbacetin, A Constituent of Ephedrae herba, Suppresses the HGF-Induced Motility of Human Breast Cancer MDA-MB-231 Cells by Inhibiting c-Met and Akt Phosphorylation", *Planta Med 79*, 1525-1530 (2013).
Ibrahim et al., "Microbial metabolism of biologically active secondary metabolites from Nerium oleader L", *Chem Pharm Bull*, 56(9), 1253-125 (2008).
Ignatenko et al., "Combination chemoprevention of intestinal carcinogenesis in a murine model of familial adenomatous polyposis", *Nutr Cancer*, 60 Suppl 1, 30-35 (2008).
Jackson et al., "X-ray structure determination of Trypanosoma brucei ornithine decarboxylase bound to D-ornithine and to G418: insights into substrate binding and ODC Conformational Flexibility", J. Biol. Chem. 278, 22037-22043 (2003).
Jacobson et al., "A hierarchical approach to all-atom protein loop prediction", *Proteins 55*, 351-367 (2004).
Jansen et al., "Tumor promoter-induced ornithine decarboxylase gene expression occurs independently of AP-1 activation", *Oncogene 18*, 5806-5813 (1999).
Je Ma et al., "Calpain inhibitory flavonoids isolated from Orostacys japonicas", *J. Enzyme Inhib Med Chem 24*(3), 676-679 (2009).
Khor et al., "Chemoprevention of famill adenomatous polyposis in Apc(Min/+) mice by phenethyl isothiocyanate (PEITC)", *Mol Carcinog 47*, 321-325 (2008).
Kombal et al., "Flavan-3-ols and flavonoids from Potentilla anserine", *Planta Med 61*(5), 484-485 (1995).
Lao et al., "Irreversible ototoxicity associated with difluoromethylornithine", *Cancer Epidemiol Biomarkers Prev 13*, 1250-1252 (2004).
Lee et al., "Antioxidatve penotic compounds rom the roots of Rhodiola sachalinensis A. Bor", *Arch Pharm Res 23*(5), 455-458 (2000).
Mandir et al., "Conjugated linoleic acids differentially alter polyp number and diameter in the Apc(min/+) mouse model of intestinal cancer", *Cell Prolif*, 41, 279-291 (2008).
Meyskens et al., "Effect of alpha-difluoromethylornithine on rectal mucosal levels of polyamines in a randomized, double-blinded trial for colon cancer prevention", *J. Natl Cancer Inst 90*, 1212-1218 (1998).
Middleton et al., "The Effects of Plant Flavonoids on Mammalian Cells: Implications for Inflammation, Heart Disease, and Cancer", *Pharmacological Reviews*, vol. 52 (4), 673-751 (2000).
Mortelmans et al., "The Ames *Salmonella*/microsome mutagenicity assay", *Mutat. Res. 455*, 29-60 (2000).
Moser et al., "A dominant mutation that predisposes to multiple intestinal neoplasia in the mouse", *Science 247* (4940), 322-324 (1990).
Mukherjee et al., "Sensitization of diabetic and obese mice to insulin by retinoid X receptor agonists", *Nature 386*, 407-410 (1997).
Osterman et al., "Formation of functional cross-species heterodimers of ornithine decarboxylase", *Biochemistry 33*, 13662-13667 (1994).
Patent Cooperation Treaty, International Searching Authority, Search Report and Written Opinion for PCT/US2012/65898, 10 pages, dated Jan. 29, 2013.
Pegg, "Polyamine metabolism and its importance in neoplastic growth and a target for chemotherapy", *Cancer Res 48*, 759-774 (1988).
Shelley et al., "Epik: a software program for pK(a) prediction and protonation state generation for drug-like molecules", *J. Comput Aided Mol Des 21*, 681-691 (2007).
Struijs et al., "The chain length of lignin macromolecule from flaxseed hulls is determined by the incorporation coumaric acid glucosides and ferulic acid glucosides", *Phytochemistry 70*(2), 262-269 (2009).

(56) References Cited

OTHER PUBLICATIONS

Struijs et al., "The flavonoid herbacetin diglucoside as a constituent of the lignin macromolecule from flaxseed hulls", *Phytochemicstry* 68(8), 1227-1235 (2007).
Sturn et al., "Genesis: cluster analysis of microarray data", *Bioinformatics 18*, 207-208 (2002).
Su et al., Multiple intestinal neoplasia caused by a mutation in the murine homolog of the APC gene [published erratum appears in Science 22; 256(5060):114] Science 256(5057): 668-670) (1992).
Tseng et al., "Lack of 12-O-tetradecanoylphorbol-13-acetate responsiveness of ornithine decarboxylase introns which have AP-1 consensus sequences", Molecular and cellular biochemistry, 146, 7-12 (1995).
Weeks et al., "Alpha Difluoromethylornithine, an irreversible inhibitor of ornithine decarboxylase, inhibits tumor promoter-induced polyamine accumulation and carcinogenesis in mouse skin", Proc Natl Acad Sci, 79, 6028-6032 (1982).
Yen et al., "Synergistic effect of a retinoid X receptor-selectve ligand bexarotene (LGD1069, Targretin) and paclaxel (Txol) in mammary carcinoma" *Breast Cancer Research and Treatment*, 88, 141-148 (2004).
Yen et al., "A selective Retinoid X Receptor Agonist Bexarotene (Targretin) Prevents and Overcomes Acquired Pacltael (Taxol) Resistance in Human Non-Small Cell Lung Cancer", *Clin. Cancer Res. 10*, 8656-8664 (2004).
Yoshimura et al., "Flavonol glucuronides and C-glucosidic ellagitannins from Lelaleuca squarrosa", *Phytochemistry 69*(1), 3062-3069 (2008).
Kim, et al., "Herbacetin is a Novel Allosteric Inhibitor of Ornithine Decarboxylase with Antitumor Activity", Cancer Res 76(5), 1146-1157 (2015).

\* cited by examiner

Figure.1 a+b+c+d+e
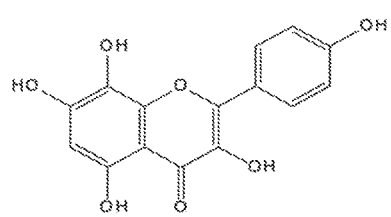 [SMILES: O=c1c(O)c(-c2ccc(O)cc2)oc2c(O)c(O)cc(O)c12]
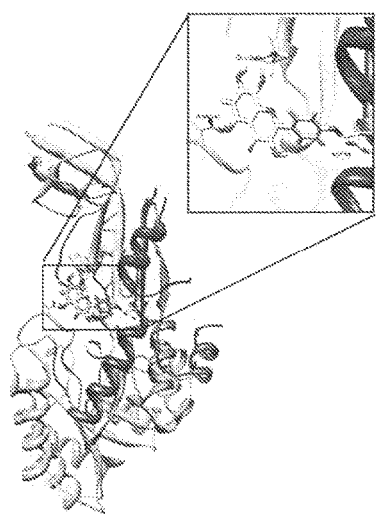
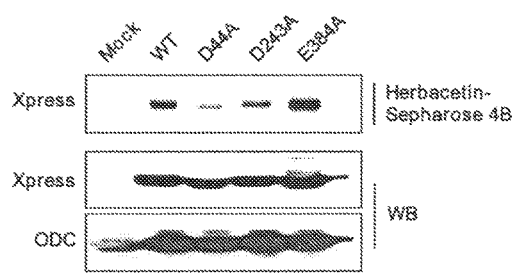
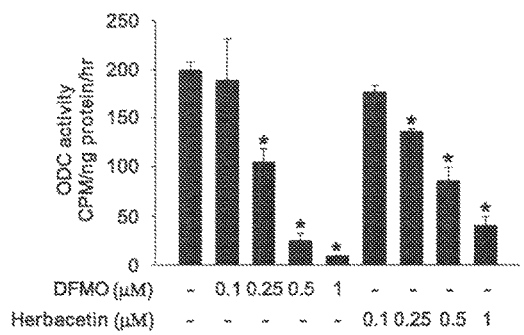

Figure.1 f+g+h
f
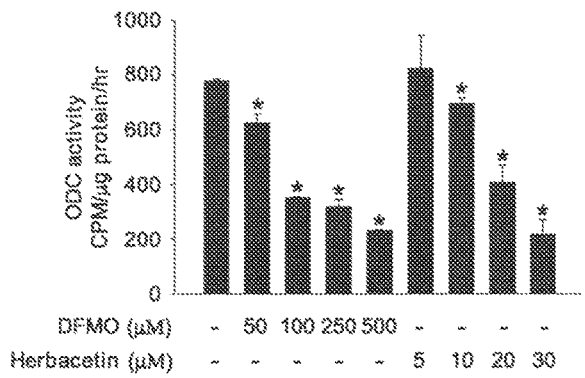
g
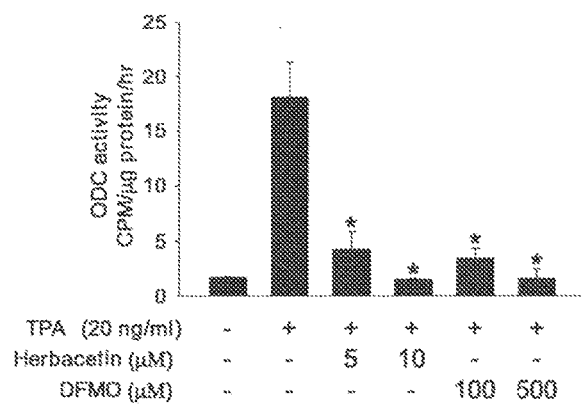
h
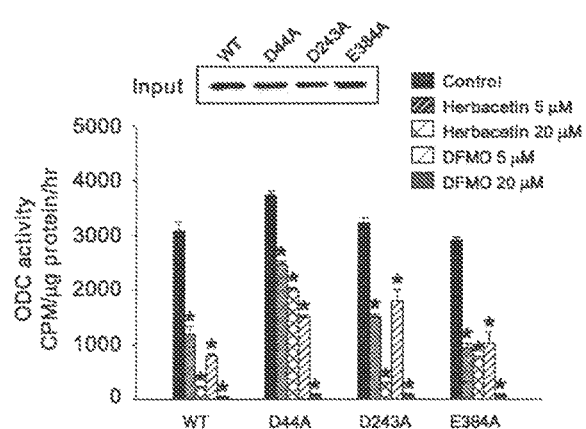

Figure.2 a+b+c+d
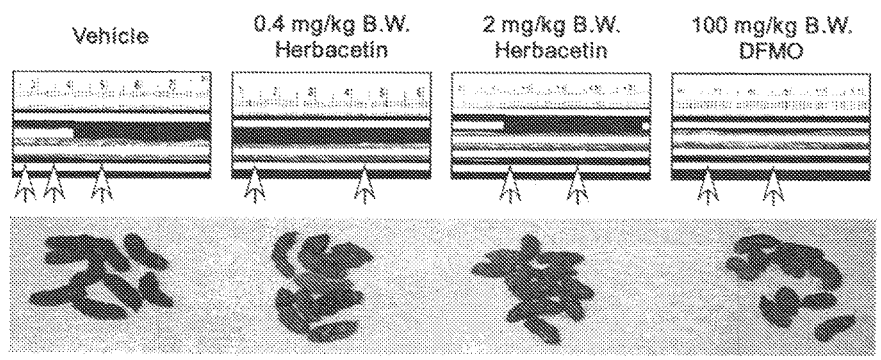
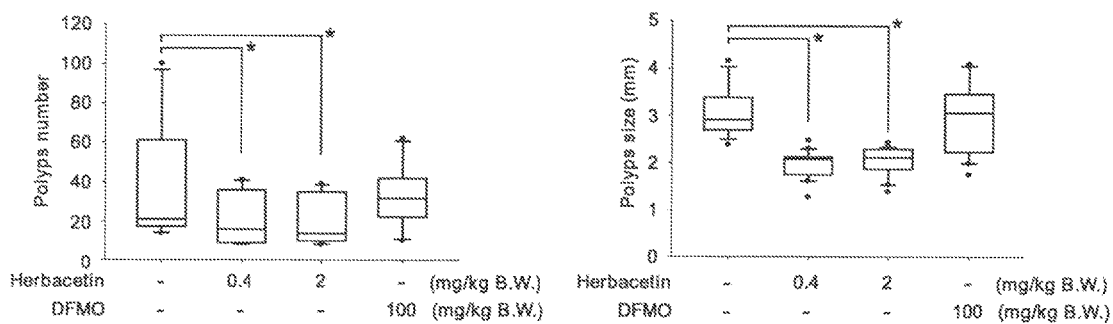
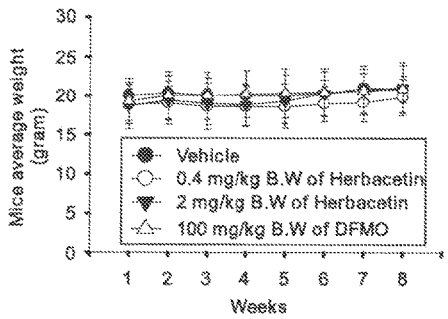

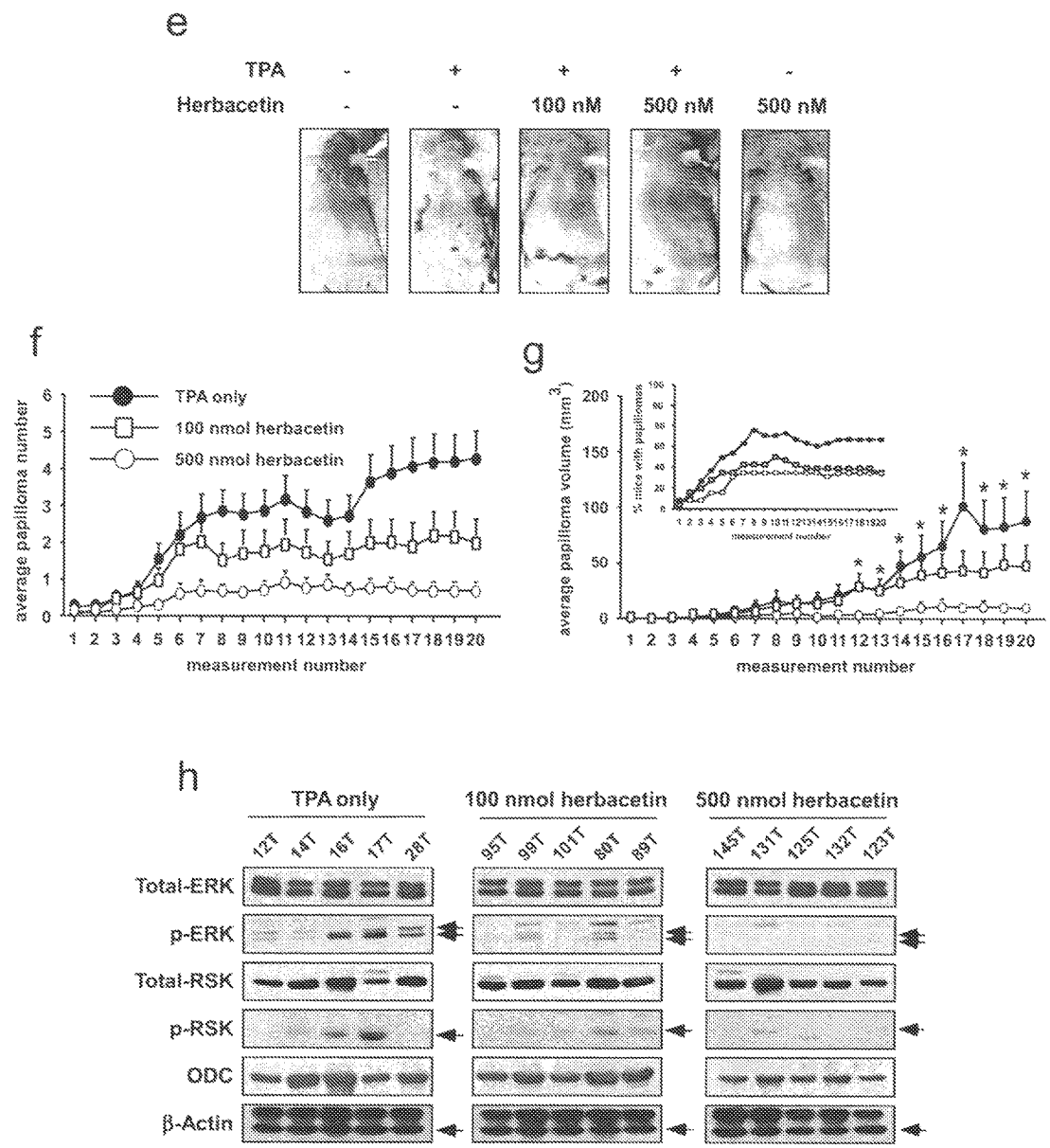
Figure 2e+f+g+h

Figure.2 i+j
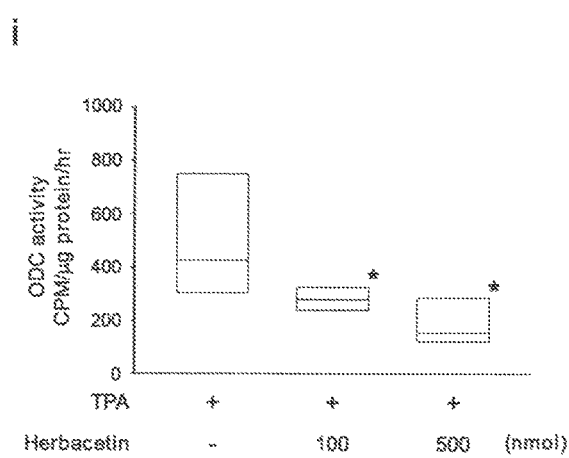
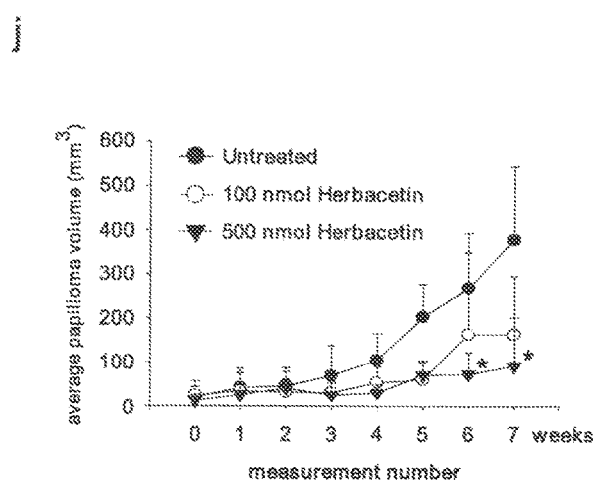

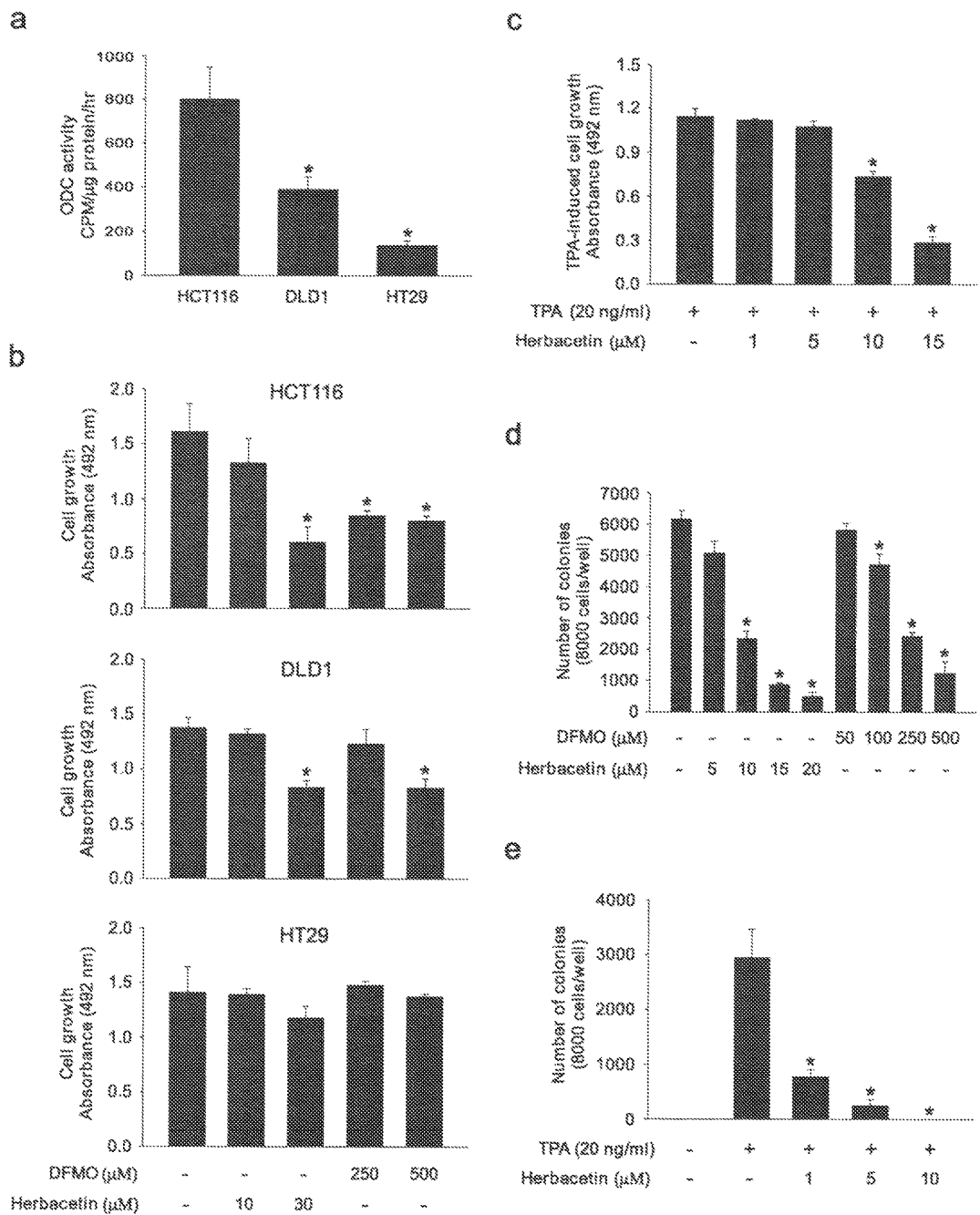

Figure.3 f+g+h
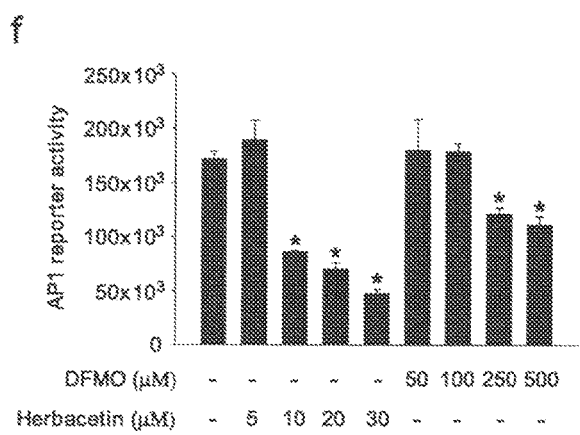
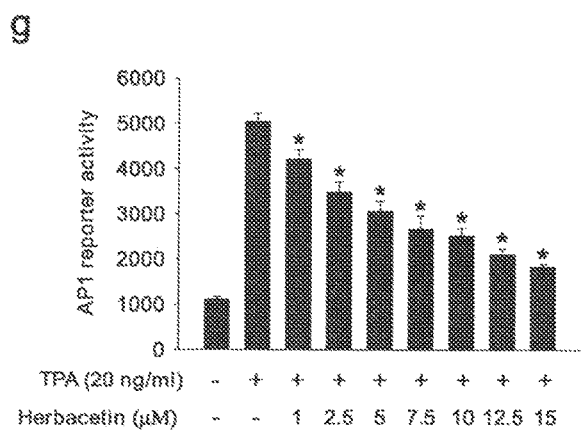
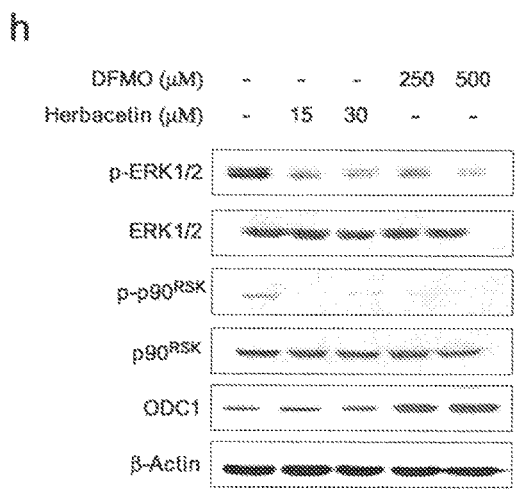

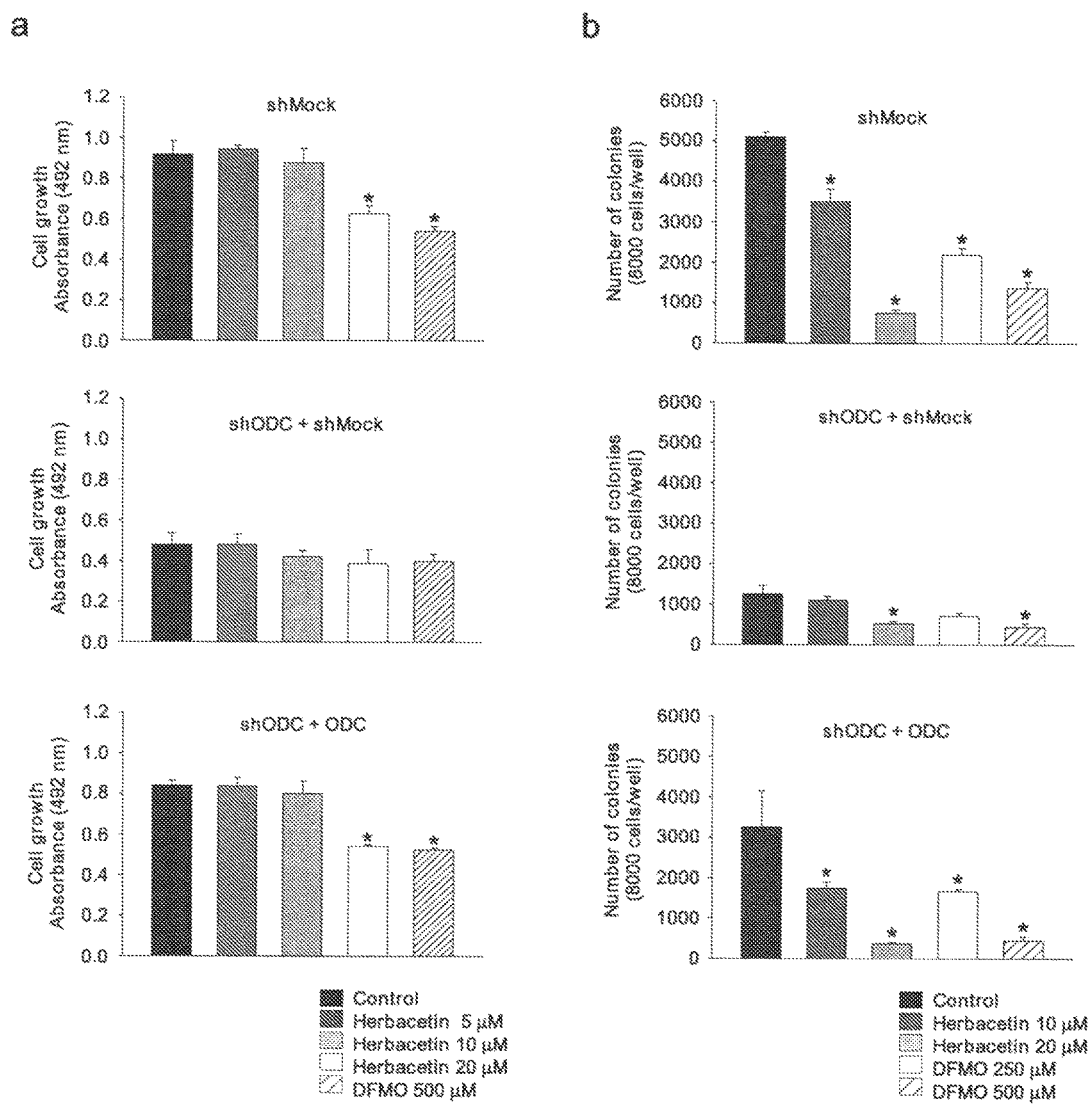
Figure.4 a+b

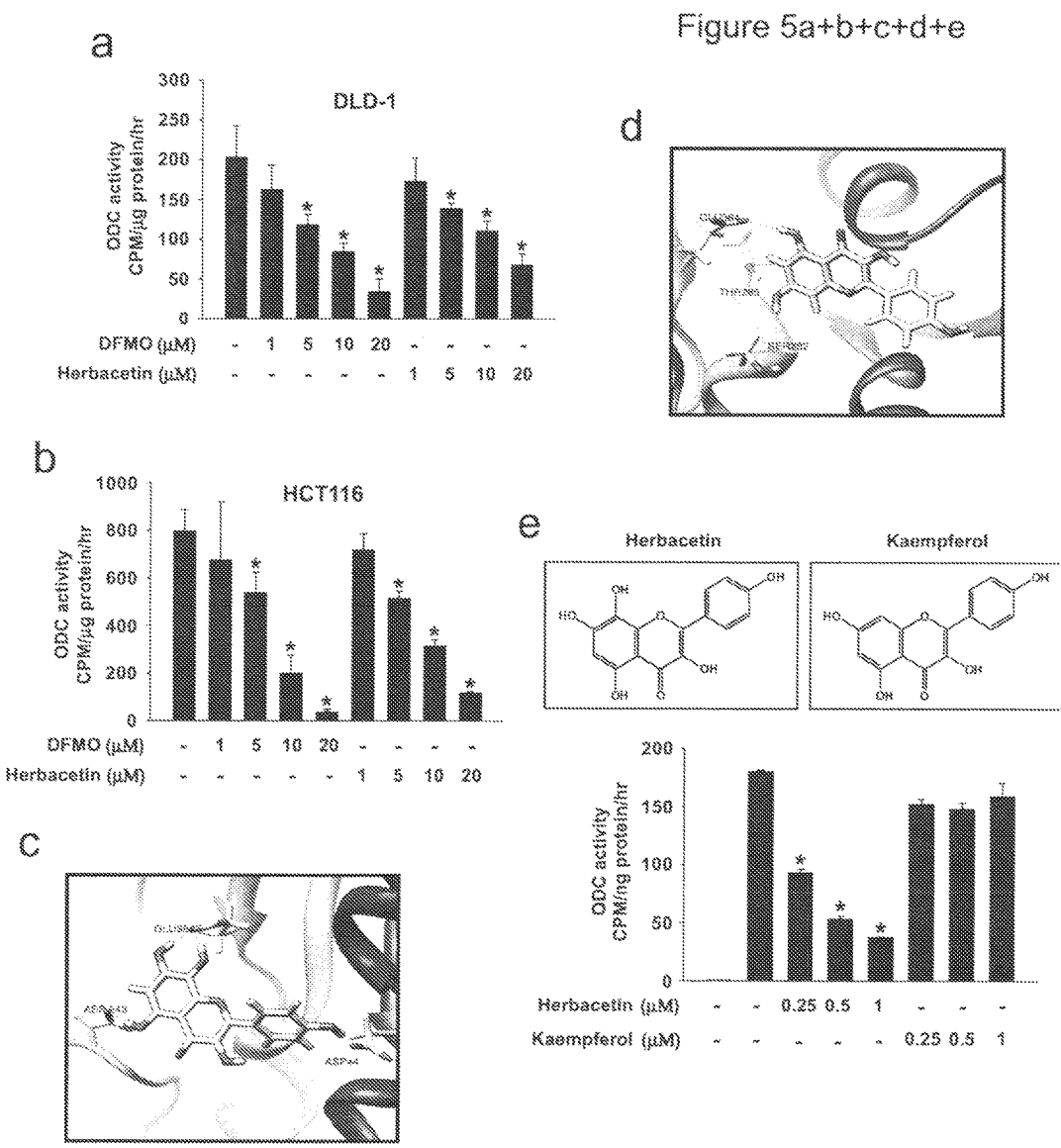
Figure 5a+b+c+d+e

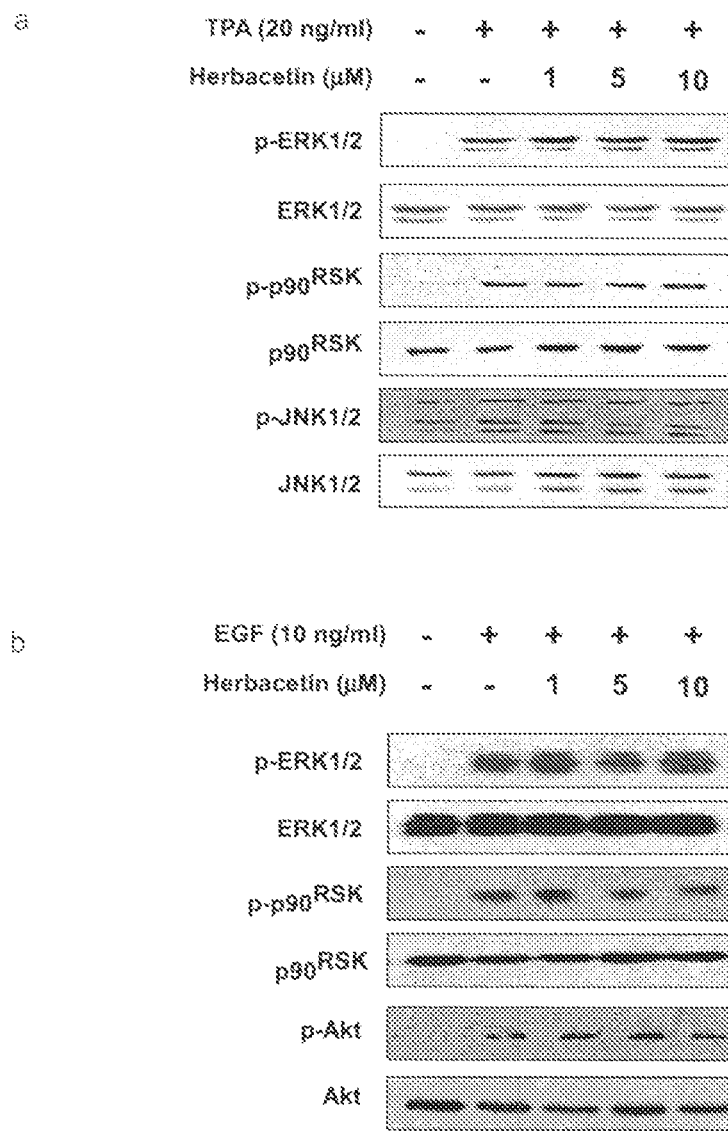
Figure 6a+b

Figure 7a+b+c+d a

1 day
2 day c

| Term | Count | P-value |
|---|---|---|
| Regulation of actin cytoskeleton | 14 | 6.80E-03 |
| Citrate cycle (TCA cycle) | 5 | 9.40E-03 |
| Pyruvate metabolism | 5 | 3.00E-02 | b

Herbacetin treated for 1 day

| Term | Count | P-value |
|---|---|---|
| Cell proliferation | 16 | 3.10E-03 |
| Cell cycle | 27 | 3.10E-03 |
| Apoptosis | 36 | 3.50E-03 |
| Cellular metabolic process | 18 | 4.10E-02 |

Herbacetin treated for 1 day

| Term | Count | P-value |
|---|---|---|
| DNA replication | 43 | 5.00E-08 |
| Cell cycle | 66 | 2.30E-06 |
| DNA repair | 34 | 7.10E-04 |
| Chromatin architecture | 38 | 9.10E-04 |
| Apoptosis | 72 | 9.10E-03 |
| Catabolic protein process | 23 | 1.40E-02 | d

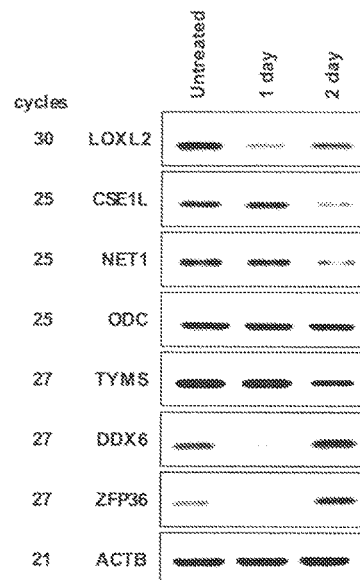

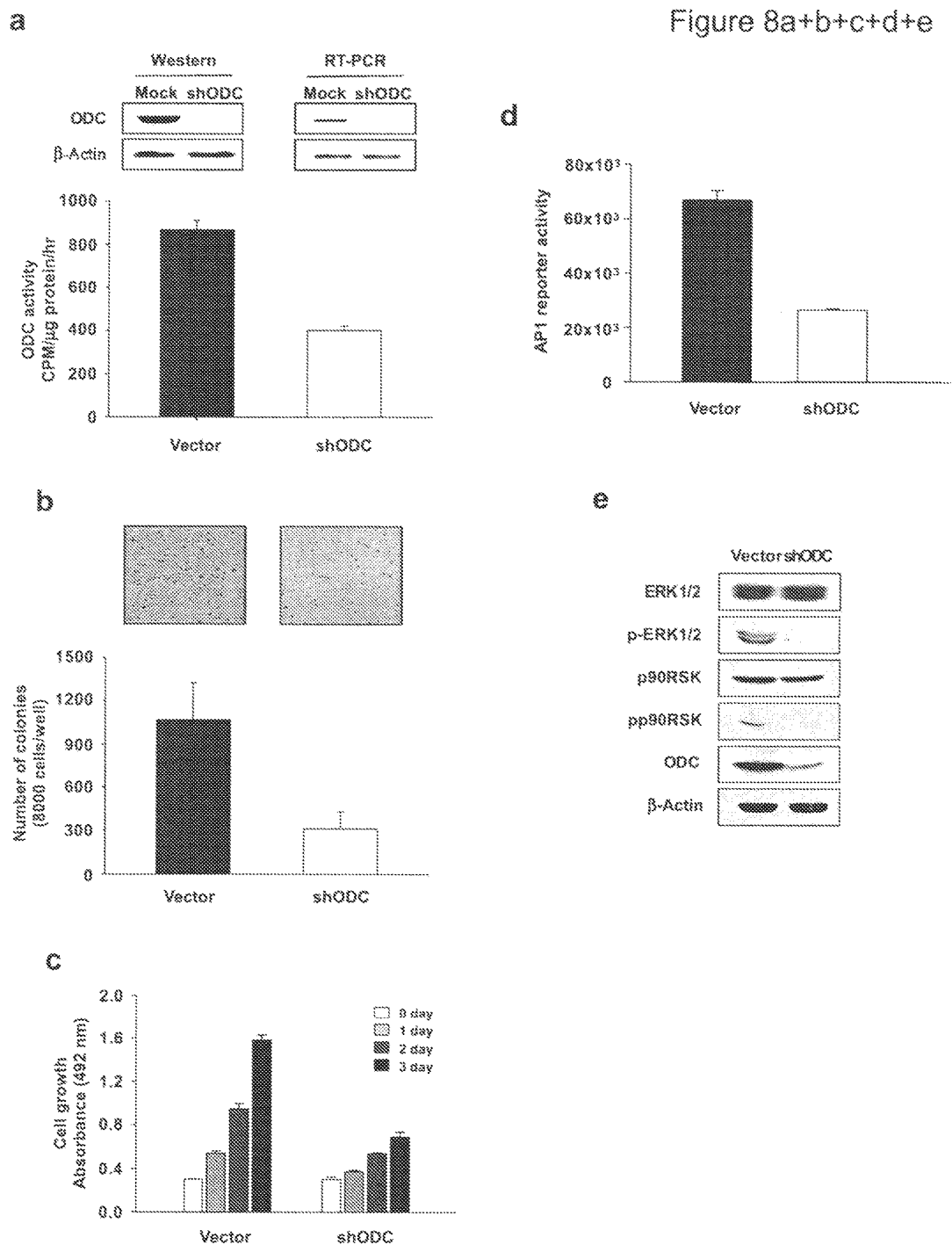

Figure 9a+b+c
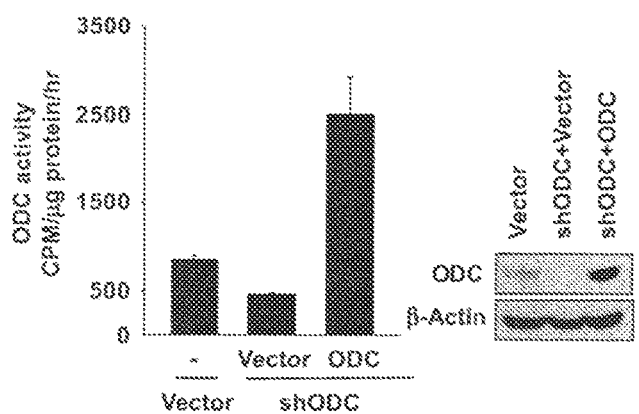
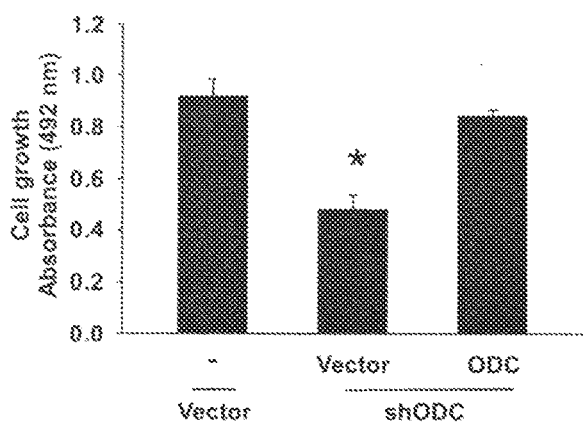
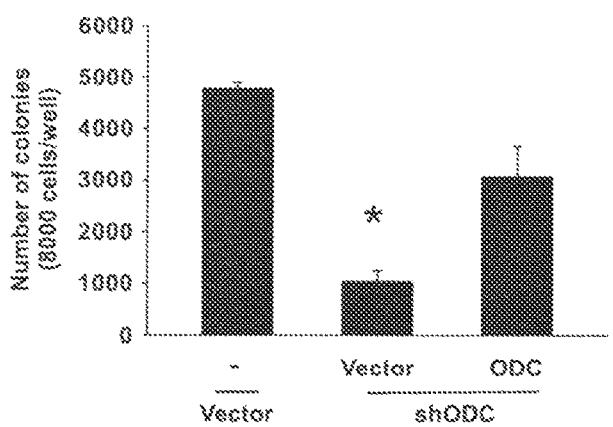

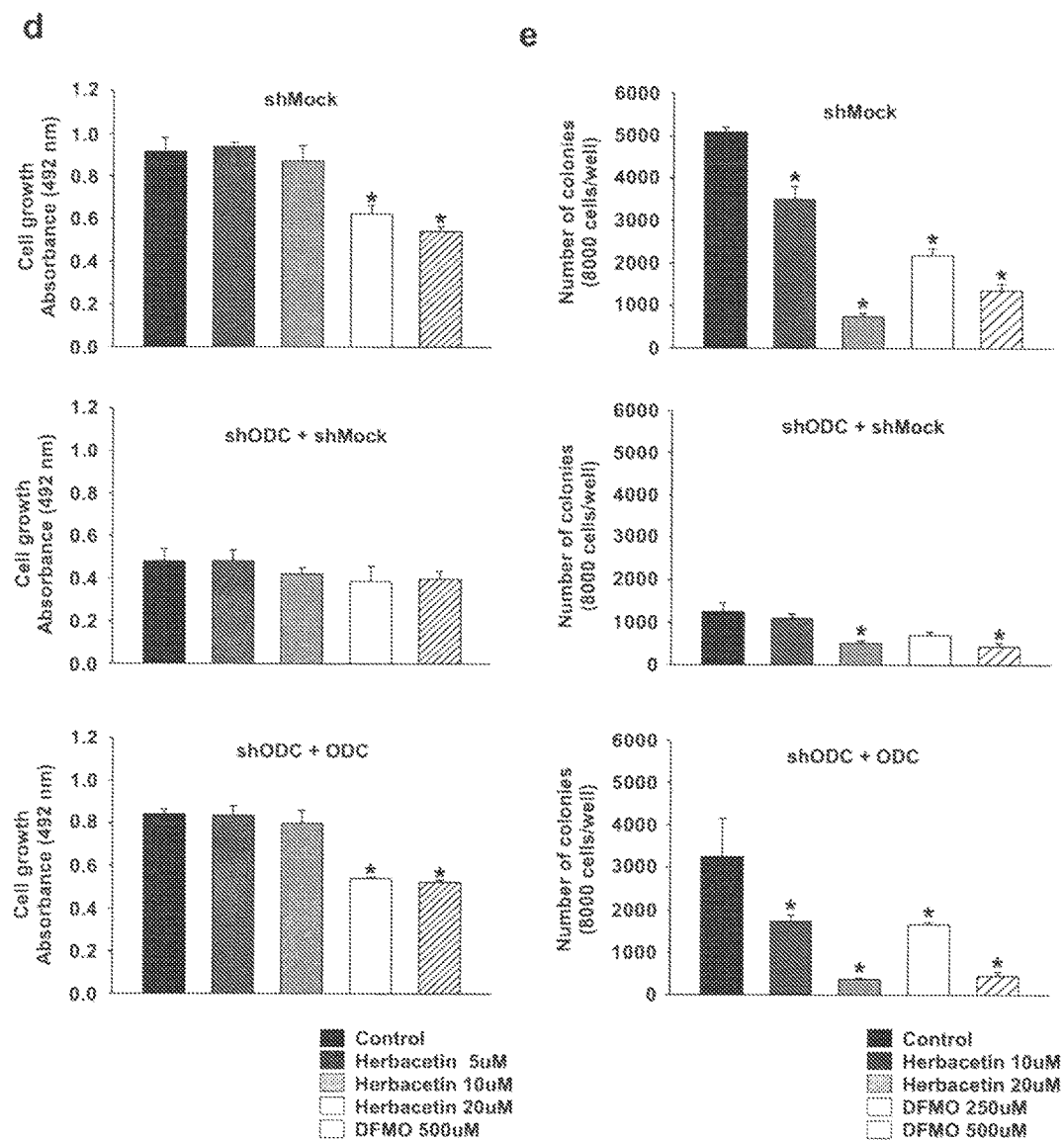
Figure 9d+e

US 10,532,040 B2

METHODS OF TREATING CANCER WITH HERBACETIN

PRIORITY OF INVENTION

This application claims priority to U.S. Provisional Application No. 61/561,436 that was filed on Nov. 18, 2011 and U.S. Provisional Application No. 61/565,320 that was filed on Nov. 30, 2011. The entire content of these provisional applications is hereby incorporated herein by reference.

GOVERNMENT FUNDING

This invention was made with government support under CA120388, R37 CA081064, ES016548 awarded by the National Institutes of Health. The government has certain rights in the invention.

BACKGROUND OF THE INVENTION

Polyamines play important roles in normal and cancer cell growth. Elevated ornithine decarboxylase (ODC) activity is observed in neoplastic tissues suggesting that this enzyme is a target for cancer prevention or treatment. Difluoromethylornithine (DFMO), an approved FDA drug, acts as an irreversible and specific ODC inhibitor. However, its activity is associated with toxicity.

Currently there is a need for additional chemical agents that are useful for treating or preventing cancer. There is also a need for anti-cancer agents that have specificity for ODC and have improved pharmacologic properties such as reduced toxicity.

SUMMARY OF THE INVENTION

The present invention provides a method for inactivating ODC in a cell comprising contacting the cell in vitro or in vivo with an effective amount of herbacetin, or a pharmaceutically acceptable salt thereof, or a pharmaceutically acceptable salt thereof.

The present invention provides a method for inhibiting cancer cell growth comprising contacting the cell in vitro or in vivo with an effective amount of herbacetin, or a pharmaceutically acceptable salt thereof.

The present invention provides a method for treating cancer in a mammal comprising administering to the mammal an effective amount of herbacetin, or a pharmaceutically acceptable salt thereof.

The present invention provides a method for treating cancer in a mammal in need of such treatment comprising administering to the mammal an effective amount of herbacetin.

The present invention provides a method for treating cancer in a mammal diagnosed with cancer comprising administering to the mammal an effective amount of herbacetin.

The present invention provides a compound comprising herbacetin, or a pharmaceutically acceptable salt thereof, for the manufacture of a medicament useful for the treatment of cancer in a mammal.

The present invention provides the use of a compound comprising herbacetin, or a pharmaceutically acceptable salt thereof, for the manufacture of a medicament useful for the treatment of cancer in a mammal.

The present invention provides a compound comprising herbacetin, or a pharmaceutically acceptable salt thereof, for use in the prophylactic or therapeutic treatment of cancer in a mammal.

The present invention provides a compound comprising herbacetin, or a pharmaceutically acceptable salt thereof, for use in the prophylactic or therapeutic treatment of cancer in a mammal.

In certain embodiments, the mammal is a human. In certain embodiments, the cancer is colon cancer or skin cancer. In certain embodiments, The present invention provides a dermal product comprising herbacetin, or a pharmaceutically acceptable salt thereof, for use in the prophylactic or therapeutic treatment skin cancer in a mammal. In certain embodiments, the product is a sunscreen. In certain embodiments, the product is a composition for treating sunburn or other sun exposure.

BRIEF DESCRIPTION OF THE FIGURES

FIGS. 1A-1H. Herbacetin binds directly to ODC and inhibits ODC activity. (a) Chemical structure of herbacetin, a new allosteric ODC inhibitor. (b) Computer modeling of herbacetin and the ODC protein crystal structure. Several hydrogen bonds are formed between herbacetin and Asp44, Asp243 and Glu384 on the backbone of ODC. (c, upper panel) Recombinant ODC, (c, lower panel) HCT116 colon cancer cell lysate or (d) ectopically expressed ODC (WT, mutant D44A, D243A and E384A) cells were incubated with herbacetin-conjugated Sepharose 4B beads or with Sepharose 4B beads alone. Proteins were pulled down using anti-Xpress and then analyzed by Western blotting. The effect of herbacetin on ODC activity was assessed using a (e) recombinant ODC protein, (f) HCT116 colon cancer cells, or (g) TPA-treated JB6 mouse skin epidermal cells. (h) The effect of herbacetin on ectopically expressed ODC (WT, D44A, D243A, E384A) activity was measured as the release of CO2 from L-[1-$C^{14}$] ornithine. For e-h, data are represented as means±S.D. of values from triplicate experiments and the asterisk (*) indicates a significant difference (p<0.05) between herbacetin- or DFMO-treated samples compared to untreated controls. WB, Western blot.

FIGS. 2A-2J. Effectiveness of herbacetin as a preventive or therapeutic agent against colon or skin cancer in vivo. (a, upper panel) Representative photographs of colons from $APC^{min}$ mice treated or not treated with herbacetin or DFMO. (a, lower panel) Representative photographs of $APC^{min}$ mice stools. (b) Number and (c) size of polyps from $APC^{min}$ mice treated or not treated with herbacetin or DFMO were calculated following euthanization. (d) Body weights from vehicle-, herbacetin- and DFMO treated groups of mice were measured once a week. (e) Representative photographs of mice subjected to the DMBA/TPA two-stage mouse skin carcinogenesis protocol and treated or not treated with herbacetin (100 or 500 nmol) followed by TPA (17 nmol). The effect of herbacetin on the (f) number and (g) volume of TPA-induced skin tumors was assessed weekly over 20 weeks. Data are represented as means±S.E. of values (n>10) and the asterisk (*) indicates a significant difference (p<0.05) between herbacetin-treated groups compared to the TPA only-treated group. No tumors were observed in the vehicle-treated or the herbacetin only—(i.e., no TPA) treated groups. Skin tissue tumors induced by TPA were isolated from vehicle- and herbacetin-treated groups of mice for immunoblot analysis of (h) ODC-target protein expression and measurement of (i) ODC activity. (j) Mice were exposed to solar-UV (48 kJ/UVA, 2.9 kJ/UVB) 3 times weekly for 12 weeks. The solar UV treatment was discontinued and at twenty weeks later, the therapeutic effect of herbacetin (100 or 500 nmol) on solar UV induced-mouse skin tumor volume was assessed weekly for 7 weeks. Data are represented as means±S.E. of values and the asterisk (*) indicates a significant difference (p<0.05) between herbacetin-treated groups compared to the vehicle-treated group.

FIGS. 3A-3H. Anticancer effect of herbacetin. (a) The effect of herbacetin on ODC activity in colon cancer cell lines was measured as the release of $CO_2$ from L-$[1-C^{14}]$ ornithine. The asterisk (*) indicates a significantly decreased (p<0.05) ODC activity in DLD1 or HT29 cells compared to HCT116 cells. (b) The effect of herbacetin and DFMO on the growth of colon cancer cells and (c) TPA-induced JB6 cell growth was compared. Cells were incubated for 72 h and growth was estimated using the MTS assay. (d) The effect of herbacetin on anchorage independent HCT116 colon cancer cell growth and (e) TPA-induced JB6 cell transformation was assessed. Cells were incubated for 2 weeks and then colonies were counted using a microscope and the Image-Pro PLUS (v.6) computer software program. The effect of herbacetin on AP-1 reporter activity in (f) HCT116 colon cancer cells and (g) TPA-induced AP-1 reporter activity in JB6 mouse epidermal cells was analyzed using the substrates included in the reporter assay system. Data are represented as means±S.D. of triplicate values from three independent experiments and the asterisk (*) indicates a significant (p<0.05) effect of herbacetin or DFMO compared to untreated or TPA-treated controls. (h) The effect of herbacetin on the phosphorylation of ERK1 and ERK2 in HCT116 colon cancer cells was determined by Western blotting. Similar results were observed from two independent experiments.

FIGS. 4A-4B. The anti-cancer activity exerted by herbacetin is dependent on ODC expression. (a) The effect of herbacetin on HCT116 colon cancer cell growth was assessed in shMock, shODC and shODC cells with rescued ODC expression. Cells were incubated for 72 h and growth was determined by MTS assay. (b) The effect of herbacetin on anchorage independent HCT116 colon cancer cell growth was assessed inshMock, shODC and shODC cells with rescued ODC expression. Cells were incubated in 0.3% agar for 3 weeks and colonies were counted using a microscope and the Image-Pro PLUS (v.6) computer software program. Data are represented as means±S.D. of triplicate values. The asterisk (*) indicates a significant effect (p<0.05) of herbacetin or DFMO compared to untreated controls.

FIGS. 5A-5E. The effect of herbacetin on ODC activity was assessed in (a) DLD-1 and (b) HCT116 colon cancer cells. Cell lysates were incubated for 15 min with reaction buffer and different doses of herbacetin or DFMO and then incubated at 37° C. for 1 h. Herbacetin (c) and kaempferol (d) were modeled as allosteric inhibitors with the ODC crystal structure. (e) The effect of herbacetin or kaempferol on ODC activity was assessed using a human ODC recombinant protein. Each reaction was incubated at 37° C. for 1 h and ODC activity was measured as the release of $CO_2$ from L-$[1-C^{14}]$ ornithine. Data are represented as means±S.D. of triplicate values. The asterisk (*) indicates a significant difference (p<0.05) between herbacetin-treated samples compared to untreated or kaempferol-treated samples.

FIGS. 6A-6B. The effect of herbacetin on (a) TPA- or (b) EGF-induced phosphorylation of ERK1 and ERK2 in JB6 mouse epidermal cells was analyzed by Western blotting. Serum-starved (0.1% FBS; 24 h) cells were treated with various doses of herbacetin for 2 h followed by treatment with TPA for 15 min. Similar results were observed in two independent experiments.

FIGS. 7A-7D. Profiling of gene expression in HCT116 colon cancer cells treated with herbacetin 1 or 2 days was assessed by microarray. Differential expression of genes induced by herbacetin was determined by using (a) hierarchical clustering and then genes were classified as up- or down-regulated according to (b) molecular function, biological process, and cellular component and (c) signaling pathway. (d) RT-PCR validation of differentially expressed genes.

FIGS. 8A-8E. Effect of knocking down ODC expression in HCT116 colon cancer cells. Colon cancer cells were stably transfected with shMock or shODC. Confirmation of (a, upper left panel) knockdown of ODC protein expression by Western blot; (a, upper right panel) knockdown of ODC transcription level by RT-PCR; and (a, lower panel) knockdown of ODC activity measured as release of L-$[1-C^{14}]$ ornithine. (b) The effect of knocking down ODC expression on anchorage-independent HCT116 colon cancer cell growth. Colonies were counted using a microscope and the Image-Pro PLUS (v6) computer software program. (c) The effect of knocking down ODC expression on HCT116 colon cancer cell growth was analyzed over 1, 2 or 3 days using the MTS assay. (d) The effect of knocking down ODC expression on AP-1 reporter activity was measured by using substrates in the reporter assay system. For a-d, data are represented as means±S.D. of triplicate values and the asterisk (*) indicates a significant difference (p<0.05) versus shMock cells. (e) Effect of knocking down ODC expression on the phosphorylation of ERK1 and ERK2 was determined by Western blotting.

FIGS. 9A-9E. The anti-cancer effects exerted by herbacetin are dependent on ODC expression. ODC activity was analyzed in HCT116 colon cancer cells expressing shMock, shODC, or sh-ODC+ODC. ODC activity (or expression) was assessed (a, left panel) as the release of L-$[1-C^{14}]$ ornithine, (a, right panel) by Western blotting, (b) by MTS assay and (c) by an anchorage independent cell growth assay. For (c), colonies were counted using a microscope and the Image-Pro PLUS (v6) computer software program. Data shown in a, b, and c are represented as means±S.D. of triplicate values and the asterisk (*) indicates a significant (p<0.05) difference versus shMock controls. d) Knockdown of ODC gives cells resistance to herbacetin (middle). ODC protein expression and ODC activity and sensitivity to herbacetin were restored with the reintroduction of ODC (shODC+ODC). Re-introduction of ODC into sh-ODC knockdown cells restored cell growth almost 70% of untransfected levels. e) Re-introduction of ODC into sh-ODC knockdown cells restored sensitivity of these cells to herbacetin or DFMO to inhibit colony growth.

DETAILED DESCRIPTION

Figure 10:
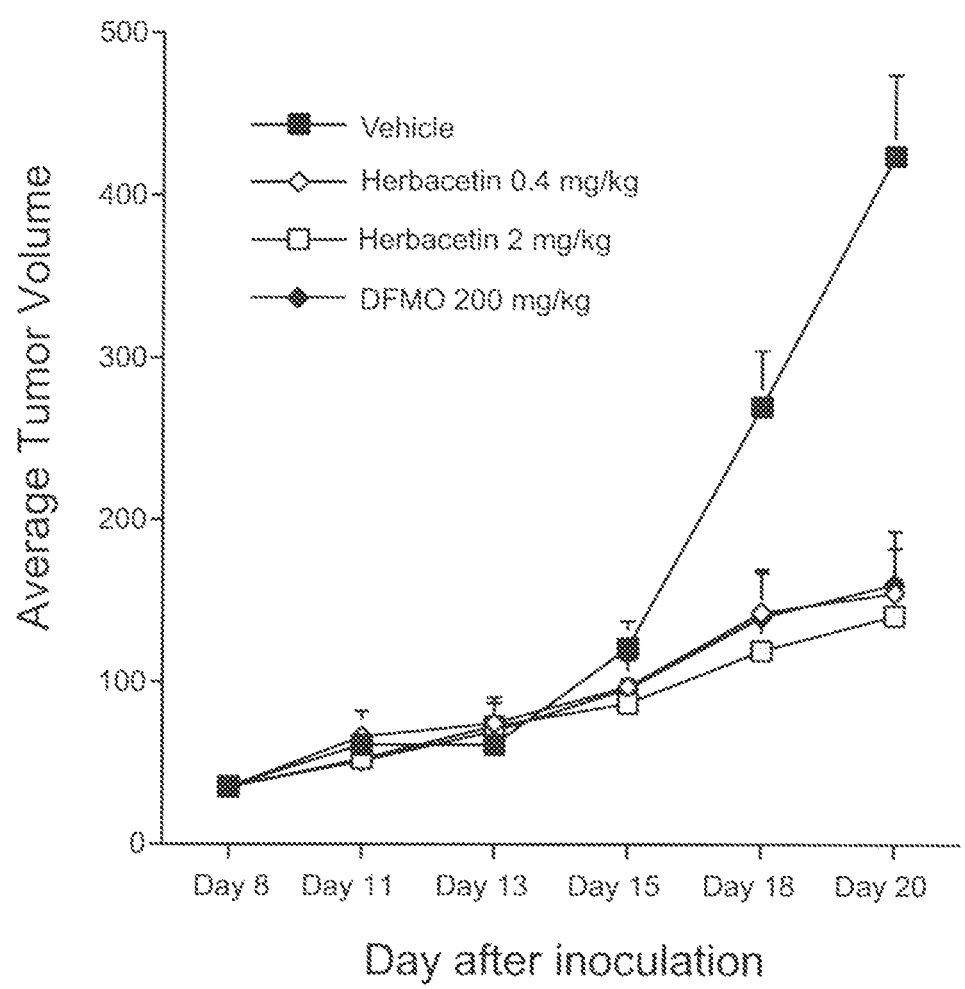
FIG. 10. Average tumor volume in Athymic nude mice inoculated with HCT116 cells.

The present invention provides a method for inactivating ODC in a cell comprising contacting the cell in vitro or in vivo with an effective amount of herbacetin, or a pharmaceutically acceptable salt thereof, or a pharmaceutically acceptable salt thereof.

The present invention provides a method for inhibiting cancer cell growth comprising contacting the cell in vitro or in vivo with an effective amount of herbacetin, or a pharmaceutically acceptable salt thereof.

The present invention provides a method for treating cancer in a mammal comprising administering to the mammal an effective amount of herbacetin, or a pharmaceutically acceptable salt thereof.

The present invention provides a method for treating cancer in a mammal in need of such treatment comprising administering to the mammal an effective amount of herbacetin.

The present invention provides a method for treating cancer in a mammal diagnosed with cancer comprising administering to the mammal an effective amount of herbacetin.

The present invention provides a compound comprising herbacetin, or a pharmaceutically acceptable salt thereof, for the manufacture of a medicament useful for the treatment of cancer in a mammal.

The present invention provides the use of a compound comprising herbacetin, or a pharmaceutically acceptable salt thereof, for the manufacture of a medicament useful for the treatment of cancer in a mammal.

The present invention provides a compound comprising herbacetin, or a pharmaceutically acceptable salt thereof, for use in the prophylactic or therapeutic treatment of cancer in a mammal.

The present invention provides a compound comprising herbacetin, or a pharmaceutically acceptable salt thereof, for use in the prophylactic or therapeutic treatment of cancer in a mammal.

In certain embodiments, the mammal is a human. In certain embodiments, the cancer is colon cancer or skin cancer.

The present invention provides a dermal product comprising herbacetin, or a pharmaceutically acceptable salt thereof, for use in the prophylactic or therapeutic treatment skin cancer in a mammal. In certain embodiments, the product is a sunscreen. In certain embodiments, the product is a composition for treating sunburn or other sun exposure.

The term "inhibiting," such as used in the phrase "inhibiting ODC" means to inhibit enzymatic activity. In certain embodiments, the ODC is inhibited by 1-100%.

The term "treatment" or "treating," to the extent it relates to a disease or condition includes preventing the disease or condition from occurring, inhibiting the disease or condition, eliminating the disease or condition, and/or relieving one or more symptoms of the disease or condition.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames Salmonella/microsome mutagenicity assay." Mutat. Res. 2000, 455, 29-60.)

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form. In certain embodiments, the dose is about 300 mg/m$^2$/day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. In certain embodiments, compounds of the invention can be administered in combination with agents that are useful for the treatment of breast cancer. (Yen, W. et al. "Synergistic effect of a retinoid X receptor-selective ligand bexarotene (LGD 1069, Targretin) and paclitaxel (Taxol) in mammary carcinoma" Breast Cancer Research and Treatment, 2004, 88, 141-148.) In certain embodiments, compounds of the invention can be administered in combination with agents that are useful for the treatment of lung cancer. (Yen, W.-C.; Corpuz, M. R.; Prudente, R. Y.; Cooke, T. A.; Bissonnette, R. P.; Negro-Vilar, A.; Lamph, W. W. "A Selective Retinoid X Receptor Agonist Bexarotene (Targretin) Prevents and Overcomes Acquired Paclitaxel (Taxol) Resistance in Human Non-Small Cell Lung Cancer." Clin. Cancer Res. 2004, 10, 8656-8664.). In certain embodiments, compounds of the invention can be administered in combination with agents that are useful for the treatment of diabetes. (Mukherjee, R.; Davies, P. J. A.; Crombie, D. L.; Bischoff, E. D.; Cesario, R. M.; Jow, L.; Hamanns, L. G.; Boehm, M. F.; Mondon, C. E.; Nadzan, A. M.; Paterniti, J. R.; Heyman, R. A. "Sensitization of diabetic and obese mice to insulin by retinoid X receptor agonists." Nature 1997, 386, 407-410.) Accordingly, in one embodiment the invention also provides a composition comprising a compound of the invention, or a pharmaceutically acceptable salt thereof, at least one other therapeutic agent, and a pharmaceutically acceptable diluent or carrier. The invention also provides a kit comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to an animal to treat cancer or diabetes.

Example 1

Herbacetin Suppresses Tumor Growth in Colon and Skin

Ornithine decarboxylase (ODC) is a first step rate-limiting enzyme in polyamine biosynthesis (Casero, R. A., Jr. & Marton, L. J. Targeting polyamine metabolism and function in cancer and other hyperproliferative diseases. *Nat Rev Drug Discov* 6, 373-390 (2007)). It is highly expressed in many cancer cell types and promotes growth and tumor formation (Gerner, E. W. & Meyskens, F. L., Jr. Polyamines and cancer: old molecules, new understanding. *Nat Rev Cancer* 4, 781-792 (2004)). Difluoromethylornithine (DFMO) is an approved FDA drug that acts as an irreversible and specific ODC inhibitor, and reportedly prevents carcinogenesis, especially in the skin and colon (Weeks, C.

E., Herrmann, A. L., Nelson, F. R. & Slaga, T. J. alphaDifluoromethylornithine, an irreversible inhibitor of ornithine decarboxylase, inhibits tumor promoter-induced polyamine accumulation and carcinogenesis in mouse skin. *Proc Natl Acad Sci USA* 79, 6028-6032 (1982); Meyskens, F. L., Jr., et al. Effect of alpha-difluoromethylornithine on rectal mucosal levels of polyamines in a randomized, double-blinded trial for colon cancer prevention. *J Natl Cancer Inst* 90, 1212-1218 (1998)). However, high doses of DFMO are associated with limiting toxicity. The purpose of this study was to identify a potent and less toxic ODC inhibitor. We used computer docking and modeling to screen allosteric ODC inhibitors and discovered herbacetin as a potent ODC inhibitor. Based on the computer docking results, we used pull-down binding assays to identify the binding site between herbacetin and ODC. Results of animal studies indicated that administration of herbacetin prevented colon tumorigenesis in the APC$^{min+}$ mouse model and suppressed skin carcinogenesis in the two-stage 7,12-dimethylbenz[a]-anthracene/12-Otetradecanoylphorbol-13-acetate-induced skin cancer mouse model. In addition, herbacetin was effective in reducing the size of solar UV-induced skin tumors, indicating a strong therapeutic effect. Cell-based assays indicated that herbacetin suppressed ODC activity markedly more effectively than DFMO. These results suggest that herbacetin is a novel ODC inhibitor that should be useful for preventing and treating cancers.

G418 was reported as an allosteric inhibitor of ODC (Jackson, L. K., Goldsmith, E. J. & Phillips, M. A. X-ray structure determination of Trypanosoma brucei ornithine decarboxylase bound to D-ornithine and to G418: insights into substrate binding and ODC conformational flexibility. *J Biol Chem* 278, 22037-22043 (2003)). To identify potential active compounds targeting this allosteric site, we performed docking studies using the Traditional Chinese Medicine Database (TCMD). Results indicated that herbacetin (FIG. 1a,b) was a potential allosteric inhibitory compound that targets ODC. Herbacetin is a novel flavonol found in natural sources such as *Linum usitatissimum* and *Roemeria hybrid* (Struijs, K., Vincken, J. P., Doeswijk, T. G., Voragen, A. G. & Gruppen, H. The chain length of lignan macromolecule from flaxseed hulls is determined by the incorporation of coumaric acid glucosides and ferulic acid glucosides. *Phytochemistry* 70, 262-269 (2009)). To examine the interaction between herbacetin and ODC, we performed in vitro pull-down assays using herbacetin-conjugated Sepharose 4B beads (or Sepharose 4B as negative control) and a recombinant ODC protein (FIG. 1c, upper panel) or a HCT116 colon cancer cell lysate (FIG. 1c, lower panel). Results confirmed that herbacetin directly binds to ODC. Furthermore, computer docking results indicated that Asp44, Asp243, and Glu384 on ODC might be involved in the binding. These sites were mutated to alanine (D44A, D243A, E384A) and ectopically expressed in HCT116 colon cancer cells. Pull-down assays using each mutant and herbacetin-conjugated Sepharose 4B revealed that the D44A mutant showed the most reduced binding affinity with herbacetin (FIG. 1d), suggesting that this site is important for binding. Next, we compared the effect of herbacetin and DFMO on ODC activity using a recombinant ODC protein (FIG. 1e), HCT116 (FIG. 1f, FIG. 5a) or DLD-1 colon cancer cell lysates (FIG. 5b), and mouse epidermal cells (FIG. 1g). Herbacetin and DFMO inhibited ODC activity similarly in vitro (FIG. 1e). However, herbacetin was markedly more effective than DFMO in suppressing ODC activity in cell-based assays (FIG. 1f, g). Furthermore, ODC activity was similar in the wildtype and mutant ODC proteins because the mutated sites originated from the allosteric binding site of ODC rather than the active site. The ODC D44A mutant activity was less susceptible to the effects of herbacetin than the other mutants (D243A, E384A) or the wildtype ODC (FIG. 1h). Additionally, we docked herbacetin in silico to a selected pocket in the 1NJJ (ODC) protein structure, which allowed not only the ligand to be flexible, but also allowed the amino acids forming the protein binding site to achieve a more realistic view of the possible protein-ligand interaction. Results indicated that herbacetin forms numerous favorable interactions and docked nicely within the ODC allosteric site, especially at residue Asp44 (1.64 Å). In contrast, a similar compound, kaempferol, could not form these interactions. In this model, important hydrogen bonds were formed between herbacetin and ODC's backbone at Asp44, Asp243 and Glu384 (FIG. 5c). In contrast, kaempferol formed hydrogen bonds at Glu384, Thr285 and Ser282 (FIG. 5d). Kaempferol had little effect on ODC activity compared to herbacetin, suggesting that the binding of herbacetin with Asp44 might be more important for inhibiting ODC activity (FIG. 5e).

Early clinical trials failed to show efficacy for DFMO as a single agent in treating various cancers (Horn, Y., Schechter, P. J. & Marton, L. J. Phase I-II clinical trial with alpha-difluoromethylornithine—an inhibitor of polyamine biosynthesis. *Eur J Cancer Clin Oncol* 23, 1103-1107 (1987); Ganju, V., Edmonson, J. H. & Buckner, J. C. Phase I study of combined alpha interferon, alpha difluoromethylornithine (DFMO), and doxorubicin in advanced malignancy. *Invest New Drugs* 12, 25-27 (1994). Lao, C. D., et al. Irreversible ototoxicity associated with difluoromethylornithine. *Cancer Epidemiol Biomarkers Prev* 13, 1250-1252 (2004)). In contrast, a combination of DFMO and sulindac was shown to have a considerable inhibitory effect on colon cancer (Bailey, H. H., et al. A randomized, double-blind, placebo-controlled phase 3 skin cancer prevention study of {alpha}-difluoromethylornithine in subjects with previous history of skin cancer. *Cancer Prev Res (Phila)* 3, 35-47 (2010)). We examined the antitumor activity of herbacetin in colon tumorigenesis and skin carcinogenesis and also its effectiveness in treating skin cancer using in vivo mouse models. ODC gene expression is up-regulated in the intestinal tissue of APC$^{min+}$ mice, a model that mimics familial adenomatous polyposis (FAP). APC$^{min+}$ mice were administered herbacetin (0.4 or 2 mg/kg body weight), DFMO (100 mg/kg body weight) or vehicle 3 times/week for 8 weeks. At the end of 8 weeks, polyp number and size were determined and stool samples collected (FIG. 2a). One phenotype of these mice is anemia, which results in bloody stools. Treatment of mice with 0.4 or 2 mg/kg of herbacetin significantly suppressed polyp number and size compared to the vehicle-treated group (FIG. 2b, c; p<0.05) and seemed to reduce anemia (FIG. 2a). DFMO had little effect on number or size of polyps. Mice tolerated treatment with herbacetin without overt signs of toxicity or significant body weight loss (FIG. 2d). Overall, herbacetin-treated mice appeared healthier than vehicle- or DFMO-treated mice. DFMO has also been suggested as a preventive agent against skin cancer (Boyd, K. E. & Farnham, P. J. Identification of target genes of oncogenic transcription factors. *Proc Soc Exp Biol Med* 222, 9-28 (1999)). Therefore, we examined the effect of herbacetin on skin carcinogenesis in the two-stage 7,12-dimethylbenz[a]-anthracene (DMBA)/12-O-tetradecanoylphorbol-13-acetate (TPA)-induced skin cancer mouse model (FIG. 2e). Treatment of mice with herbacetin strongly suppressed the number and volume of skin tumors relative to the TPA-treated group (FIG. 2f-g; p<0.05), ODC downstream proteins such as ERK and RSK (FIG. 2h) and also significantly inhibited ODC activity (FIG. 2i). Furthermore we examined the possible therapeutic effect of herbacetin on solar-UV induced skin tumors in SKH-1 hairless mice. Tumors were induced by exposure of mice to solar UV for 12 weeks. Solar UV was discontinued to allow tumor development and at twenty weeks later, tumors were treated with herbacetin (100 or 500 nmol) for an additional 7 weeks. Results indicated that herbacetin significantly decreased the size (i.e., volume) of skin tumors relative to the vehicle group (FIG. 2j; p<0.05). These results indicated that herbacetin is a potent ODC inhibitor and an active anticancer agent against colon and skin cancer. Previous reports indicate that ODC activity is regulated by the proto-oncogene c-myc as a target of 13-catenin (Jansen, A. P., Colburn, N. H. & Verma, A. K. Tumor promoter-induced ornithine decarboxylase gene expression occurs independently of AP-1 activation. *Oncogene* 18, 5806-5813 (1999)) or tumor promoter TPA (Tseng, C. P. & Verma, A. K. Lack of 12-O-tetradecanoylphorbol-13-acetate responsiveness of ornithine decarboxylase introns which have AP-1 consensus sequences. *Molecular and cellular biochemistry*, 146, 7-12 1995). We measured ODC activity in HCT116, DLD1, and HT29 colon cancer cells and determined that, of the three, HCT116 cells had the highest ODC activity (FIG. 3a). We compared the effect of herbacetin and DFMO on the growth of each colon cancer cell line (FIG. 3b) and also examined its effect on growth of TPA-induced JB6 mouse skin epidermal cells (FIG. 3c). The findings indicated that herbacetin had the greatest inhibitory effect on colon cancer cells that expressed higher levels of ODC. We also examined the effect of herbacetin on anchorage independent HCT116 colon cancer cell growth and TPA-induced JB6 cell transformation.

Herbacetin was at least 20-fold more effective than DFMO in suppressing anchorage independent growth of HCT116 colon cancer cells (FIG. 3d) and also markedly suppressed TPA-induced neoplastic transformation of JB6 epidermal cells (FIG. 3e).

A previous study demonstrated that polyamines regulate signal transduction from the cell membrane to the nucleus by activating MAP kinases, including Ras, MEKs and ERKs (Pegg, A. E. Polyamine metabolism and its importance in neoplastic growth and a target for chemotherapy. *Cancer Res* 48, 759-774 (1988)). We determined whether herbacetin affected the reporter activity of the MAP kinase target transcription factor, activator protein-1 (AP-1), in HCT116 cells or JB6 cells stimulated with TPA. HCT116 cells were treated with herbacetin for 48 hand JB6 cells were pre-treated with herbacetin for 2 h before stimulation with TPA for 48 h. AP-1 reporter activity was then measured (FIG. 3f, g) and the activity was attenuated by herbacetin in colon cancer cells and in TPA-activated JB6 cells. Treated cells were also subjected to Western blotting and herbacetin also suppressed phosphorylation of ERK1/2 as well as p90$^{RSK}$ (FIG. 3h). We next examined whether herbacetin directly suppresses phosphorylation of ERK1/2. JB6 cells were treated with TPA or EGF for 15 min after pre-treatment with herbacetin for 2 h and protein expression was analyzed by Western blotting (Supplementary FIG. 2a,b). Results indicated that herbacetin decreases ODC activity resulting in attenuated AP-1 activation. However, the inhibition does not occur directly through the suppression of ERKs/RSK2 signaling.

To identify genes potentially regulated by herbacetin, we analyzed gene expression in HCT116 colon cancer cells by cDNA microarray. The differentially-expressed genes were selected using hierarchical clustering (correlation>0.9) and the genes were classified by molecular functions and signaling pathways using the DAVID database (FIG. 6a-c). Results indicated that herbacetin significantly altered genes involved in proliferation, cell cycle, apoptosis and metabolic processes. Additionally, some results were confirmed using the reverse transcription polymerase chain reaction (RT-PCR) (FIG. 7d). These findings suggested that ODC plays an important role in proliferation, apoptosis and metabolic processes in cancer cells and that herbacetin can disrupt it activity and signaling.

Previous studies indicated that some cancers are regulated in an ODC expression-dependent manner (Holtta, E., Sistonen, L. & Alitalo, K. The mechanisms of ornithine decarboxylase deregulation in c-Ha-ras oncogene-transformed NIH 3T3 cells. *J Biol Chem* 263, 4500-4507 (1988); Auvinen, M., Paasinen, A., Andersson, L. C. & Holtta, E. Ornithine decarboxylase activity is critical for cell transformation. *Nature* 360, 355-358 (1992); Osterman, A., Grishin, N. V., Kinch, L. N. & Phillips, M. A. Formation of functional cross-species heterodimers of ornithine decarboxylase. *Biochemistry* 33, 13662-13667 (1994)). To study the influence of ODC expression on cancer cell growth, we constructed HCT116 cells stably expressing mock (shMock) or knockdown of ODC (shODC) (FIG. 8a-e). We also constructed stable shODC HCT116 cells with rescued expression of ODC (shODC+ODC; FIG. 9a-c). Results indicated that colon cancer cell growth is dependent on ODC expression (FIGS. 8a-e and 9a-c). We then examined the effect of herbacetin or DFMO on growth of shMock, shODC and shODC+ODC HCT116 cells. Data indicated that cells expressing shODC were resistant to herbacetin's inhibitory effect on anchorage-dependent and -independent cell growth compared to cells expressing shMock (FIG. 4a,b, middle panels). The shODC cells expressing rescued ODC regained sensitivity to herbacetin (FIG. 4a,b, bottom panels). These findings suggested that the anticancer activity exerted by herbacetin is dependent on ODC.

In summary, herbacetin interacts with Asp44, Asp243, and Glu384 on the ODC backbone and the Asp44 residue appears most important for the inhibitory effect. Herbacetin significantly suppresses colon tumorigenesis in the APC$^{min+}$ mouse and in the DMBA/TPA-induced mouse skin carcinogenesis model. It also shows a therapeutic effect on solar UV-induced skin cancer growth. Inhibition of ODC activity by herbacetin decreases AP-1 activity and the anticancer activity of herbacetin is dependent on the expression of ODC.

Methods

Lentiviral Infection.

The lentiviral expression vectors, including pLKO.1-shODC and packaging vectors, including pMD2.0G and psPAX, were purchased from Addgene Inc. (Cambridge, Mass.). To prepare ODC viral particles, each viral vector and packaging vectors (pMD2.0G and psPAX) were transfected into HEK293T cells using JetPEI following the manufacturer's suggested protocols. The transfection medium was changed at 4 h after transfection and then cells were cultured for 36 h. The viral particles were harvested by filtration using a 0.45 mm sodium acetate syringe filter and then combined with 8 μg/ml of polybrane (Millipore, Billerica, Mass.) and infected into 60% confluent HCT-116 cells overnight. The cell culture medium was replaced with fresh complete growth medium for 24 h and then cells were selected with 1.5 μg/ml of puromycine for 36 h. The selected cells were used for experiments.

ODC Enzyme Assay.

ODC activity was measured as the release of $CO_2$ from L-$[1-C^{14}]$ ornithine as previously described (Berman, H. M., et al. The Protein Data Bank. *Nucleic Acids Res* 28, 235-242).

Pull-Down Assay Using CNBr-Herbacetin-Conjugated Beads.

A recombinant human ODC protein (200 ng) or total cell lysates (500 µg) to were incubated with herbacetin Sepharose 4B (or Sepharose 4B only as a control) beads (50 µl, 50% slurry) in reaction buffer (50 mM Tris pH 7.5, 5 mM EDTA, 150 mM NaCl, 1 mM DTT, 0.01% NP40, 2 µg/mL bovine serum albumin). After incubation with gentle rocking overnight at 4° C., the beads were washed 5 times with buffer (50 mM Tris pH 7.5, 5 mM EDTA, 150 mM NaCl, 1 mM DTT, 0.01% NP40) and binding was determined by Western blotting.

Computer Docking Model.

The structure of ODC (PDB code:1NJJ) is an X-ray diffraction structure with a resolution of 2.45 Å. We used this as the receptor model in our docking program. Before docking, the ODC protein was prepared for docking following the standard procedure outlined in the Protein Preparation Wizard (Shelley, J. C., et al. Epik: a software program for pK(a) prediction and protonation state generation for drug-like molecules. *J Comput Aided Mol Des* 21, 681-691 (2007)) included in the Schrödinger Suite 2010 (Jacobson, M. P., et al. A hierarchical approach to all-atom protein loop prediction. *Proteins* 55, 351-367 (2004); Friesner, R. A., et al. Glide: a new approach for rapid, accurate docking and scoring [1. Method and assessment of docking accuracy. *Journal of medicinal chemistry*, 47, 1739-49.]). The binding pocket was selected by the G418 ligand, which was already bound to the crystal structure chosen. The Traditional Chinese Medicine Database (TCMD), which contains more than 7,500 compound constituents from 352 different herbs, animal products and minerals, was chosen as the ligand database for docking against the ODC protein structure using the Schrödinger docking program Glide (Friesner, R. A., et al. Glide: a new approach for rapid, accurate docking and scoring [1. Method and assessment of docking accuracy. *Journal of medicinal chemistry*, 47, 1739-49.]). One hundred compounds were chosen based on the docking score obtained by HTVS (high throughput virtual screening). This group was narrowed to 10 compounds based on SP (standard precision) and XP (extra precision) flexible docking.

cDNA Microarray.

RNA samples from cells treated or not treated for 1 or 2 days with herbacetin were used. Data were analyzed using hierarchical clustering and the DAVID database as previously described (Sturn, A., Quackenbush, J. & Trajanoski, Z. Genesis: cluster analysis of microarray data. *Bioinformatics* 18, 207-208 (2002); Huang da, W., Sherman, B. T. & Lempicki, R. A. Systematic and integrative analysis of large gene lists using DAVID bioinformatics resources. *Nat Protoc* 4, 44-57 (2009)).

In Vivo Studies Using the APC$^{min+}$ Mouse Model.

Male C57BL/6J$^{(Min/+)}$ mice were obtained from Jackson Laboratory and maintained under "specific pathogen-free" conditions according to the guidelines established by the University of Minnesota Institutional Animal Care and Use Committee. APC$^{min+}$ male mice were bred with C57BL/6J APC wildtype female mice. The progeny were genotyped by PCR assay to determine whether they were heterozygous for the min allele or were homozygous wildtype. APC$^{min+}$ male or female progeny were randomly assigned to groups after weaning at 3 weeks. Mice (5~6 weeks old) were divided into 4 groups: 1) untreated vehicle group (n=12); 2) mice treated with 0.4 mg herbacetin/kg of body weight (n=13); 3) mice treated with 2 mg herbacetin/kg of body weight (n=13); and mice treated with 100 mg difluoromethylornithine (DFMO)/kg of body weight (n=10). Herbacetin, DFMO, or vehicle was injected 3 times a week for 8 weeks.

In Vivo Studies Using the DMBA/TPA Two-Stage Skin Carcinogenesis Mouse Model.

Hairless SKH:HR-1-hrBr (SKH-1) mice were obtained from Charles River and were maintained under "specific pathogen-free" conditions following the guidelines established by the University of Minnesota Institutional Animal Care and Use Committee. Mice (8~9 weeks old) were divided into five groups: 1) DMBA+vehicle group (n=20); 2) DMBA-initiated (200 nmol) and TPA-promoted group (17 nmol; n=20); 3) DMBA/TPA+100 nmol of herbacetin (n=20) group; 4) DMBA/TPA+500 nmol of herbacetin group (n=20); 5) DMBA+500 nmol of herbacetin group (n=20). One week after initiation, 17 nmol of TPA in acetone was topically applied twice weekly until the termination of the experiment at 20 weeks. When used, each dose of herbacetin was dissolved in 0.2 ml of 10% $H_2O$ in acetone and then topically applied to dorsal mouse skin at 30 min before TPA treatment. The number and volume of tumors per mouse was recorded weekly. The results are expressed as the percent of mice with tumors (incidence), average tumor volumes (size) and average number of tumors per mouse (multiplicity).

In Vivo Studies Using the Solar UV Induced-Skin Tumor Mouse Model.

Mice were exposed to solar-UV (48 kJ/UVA, 2.9 kJ/UVB) 3 times weekly for 12 weeks. The solar UV treatment was discontinued and at twenty weeks later, mice were topically treated with 100 or 500 nmol of herbacetin (in acetone) for an additional 7 weeks. Mice (8-9 weeks old) were divided into three groups: 1) solar UV+vehicle group (n=4); 2) solar UV+100 nmol of herbacetin (n=4) group; 3) solar UV+500 nmol of herbacetin (n=4). The volume of tumors per mouse was recorded weekly.

Statistical Analysis.

All quantitative results are expressed as mean values±S.D. or ±S.E. Significant differences were compared using the Student's t test or one-way analysis of variance (ANOVA). A p value of <0.05 was considered to be statistically significant.

Example 2

Many components derived from dietary or medicinal plants possess substantial chemopreventive properties. Herbacetin (3,5,7,8,4'-Pentahydroxyflavone; 304.252 g/mol) is an aromatic organic compound with the molecular formula C15H12O7. It occurs naturally in flaxseed. Our preliminary data indicate that herbacetin can 1) bind to ornithine decarboxylase (ODC); 2) inhibit TPA-induced ODC1 activity; 3) suppress promoter activities of activator protein-1, Cox2, NF-kappaB; 4) decrease cell proliferation and anchorage independent colony formation of JB6 mouse epidermal skin cells. We have completed one skin cancer prevention animal study and pilot colon cancer studies.

Skin Cancer Prevention:

For the effect of herbacetin on preventing TPA-induced skin cancer, SKH-1 hairless mice were divided into 5 groups of 26-30 mice/group. All mice were initiated with 200 nmol DMBA applied topically on the dorsal surface. Two weeks later, TPA (17 nmol) was applied topically on the dorsal surface twice a week for a total of 30 weeks. Four groups of mice were treated with herbacetin (20, 100, 200, or 500 nmol) 30 min before application of TPA. Results indicated that herbacetin decreased tumor growth induced by TPA.

Colon Cancer Prevention:

Colorectal carcinoma is the second leading cause of cancer mortality, and the molecular pathways of carcinogenesis of colorectal carcinoma remain incompletely understood. Our purpose is to determine whether consumption of the natural compound, herbacetin, in drinking water will prevent colon carcinogenesis in vivo. This is based on our preliminary data and hypothesis that herbacetin possesses anti-colon tumor promoting activity in the APCMin mouse. Many components derived from dietary or medicinal plants possess substantial chemopreventive properties. Herbacetin (3,5,7,8,4'-Pentahydroxyflavone; 304.252 g/mol) is an aromatic organic compound with the molecular formula $C_{15}H_{12}O_7$. It occurs naturally in flaxseed. Our preliminary data indicate that herbacetin can 1) bind to ornithine decarboxylase (ODC); 2) inhibit TPA-induced ODC1 activity; 3) suppress promoter activities of activator protein-1; and 4) decrease proliferation and anchorage independent cell growth of several colon cancer cell lines. We have tested the effectiveness of herbacetin compared to DFMO in preventing colon cancer development in the C57BL/6J-ApcMin+ mouse strain, which is highly susceptible to spontaneous intestinal adenoma formation. DFMO is well known to prevent colon cancer in mice and humans but longterm use causes hearing loss in humans. Herbacetin might be a viable alternative without the side effects of hearing loss. Our data indicate that this compound is 20-50 times more potent than DFMO, making the probability of toxicity much less.

The C57BL/6J-ApcMin+ strain is highly susceptible to spontaneous intestinal adenoma formation. Homozygous mice are not viable. An initial report showed that one hundred percent of the C57BL/6JApcMin heterozygous mice raised on a high fat diet develop in excess of 30 adenomas throughout the intestinal tract and most die by 120 days of age. Heterozygotes also develop anemia (Moser A R; Pitot H C; Dove W F. 1990. A dominant mutation that predisposes to multiple intestinal neoplasia in the mouse. Science 247(4940):322-4; Su L K; Kinzler K W; Vogelstein B; Preisinger A C; Moser A R; Luongo C; Gould K A; Dove W F. 1992. Multiple intestinal neoplasia caused by a mutation in the murine homolog of the APC gene [published erratum appears in Science 1992 May 22; 256(5060):1114] Science 256(5057):668-70. A small number of C57BL/6J-ApcMin heterozygous female mice develop mammary tumors. The Min mutation was discovered in the progeny of a C57BL/6J male mutagenized by ethylnitrosourea. The founding (AKR×C57BL/6J) F1 female displayed circling behavior and was mated to a C57BL/6J male. Some progeny from this backcross developed adult onset anemia and intestinal adenomas. The circling behavior was determined to be a separate heritable trait and was eliminated through subsequent crosses to C57BL/6J. This strain was imported into The Jackson Laboratory in 1992. This mouse model is a well-accepted model to study colon carcinogenesis (Ignatenko, N. A., Besselsen, D. G., Stringer, D. E., Blohm-Mangone, K. A., Cui, H. and Gerner, E. W. (2008) Combination chemoprevention of intestinal carcinogenesis in a murine model of familial adenomatous polyposis. Nutr Cancer, 60 Suppl 1, 30-5. Khor, T. O., Cheung, W. K., Prawan, A., Reddy, B. S. and Kong, A. N. (2008) Chemoprevention of familil adenomatous polyposis in Apc(Min/+) mice by phenethyl isothiocyanate (PEITC). Mol Carcinog, 47, 321-5; Mandir, N. and Goodlad, R. A. (2008) Conjugated linoleic acids differentially alter polyp number and diameter in the Apc(min/+) mouse model of intestinal cancer. Cell Prolif, 41, 279-91).

ODC (ornithine decarboxylase) catalyzes the first step of cellular polyamine biosynthesis, the formation of putrescine from ornithine. Elevated ODC activity is associated with transformation caused by oncogenic Ras, v-Src, activated RhoA, and overexpression of eIF4E. The transformed phenotype can be reversed by the inhibition of ODC. ODC overexpression alone can induce a transformation in NIH-3T3 cells. ODC transcription is regulated positively by c-Myc, c-Fos and Sp1. ODC and polyamine content are increased in many cancers such as the skin and colon. In human colonic mucosal tissue, ODC is negatively regulated by the adenomatous polyposis coil (APC) tumor-suppressor gene.

Herbacetin has not been reported as having anti-cancer properties. It is found in the following plants: 1) *Orostachys japonicas*, 2) *Nerium oleander L.*, 3) *Melaleuca squarrosa*, 4) *Gardenia aubryi*, 5) flaxseed, and 6) *Potentilla anserine*.

DFMO (difluoromethylornithine) is a specific inhibitor against ODC and binds to the active site of ODC (Cys360).—DFMO (1-5 mM) treatment results in a time-dependent decrease in ODC activity and in intracellular putrescine concentration. In human colon carcinoma cells, the inhibition of ODC by DFMO is associated with decreased transcription of the growth-related c-myc and c-fos genes. DFMO and NSAIDs are potent inhibitors of colon and intestinal cancer development. Early clinical trials with DFMO were disappointing because the high doses (1-5 mM) were associated with several side effects, including abdominal pain and ototoxicity (hearing loss, vertigo, and tinnitus). Compared to DFMO, herbacetin inhibits ODC activity more effectively (FIGS. 1A-1H).

The effect of knockdown of ODC on carcinogenesis is shown in FIGS. 11A-11E. ([A] HCT116 cells were transfected (retroviral) with sh-Mock or sh-ODC and knockdown of ODC protein (left) and gene (right) expression were confirmed by Western blot or RTPCR, respectively. (B) Knockdown of ODC inhibits HCT116 colony growth in soft agar compared to mock cells. (C) Knockdown of ODC inhibits HCT116 cell growth compared to mock cells. (D) Knockdown of ODC inhibits HCT116 AP-1 reporter activity compared to mock cells. (E) Knockdown of ODC inhibits ERKs signaling in HCT116 cells compared to mock cells.

It has also been shown that Herbacetin can regulate ODC activity (FIGS. 12A-12E). For this set of experiments, ODC was re-introduced (i.e., rescue experiment) into HCT116 cells expressing sh-ODC (knockdown).

The anti-cancer effect of herbacetin in vivo has also been shown. Herbacetin prevents colon cancer development in APCMin+mice. C57BL/6J-ApcMin+ were divided into five groups and injected IP with vehicle or 1 of 2 amounts of herbacetin in vehicle. The doses included 0, 0.4, or 2 mg/kg B.W. herbacetin injected IP (n=15 total, 5 per group; Table 1). APC-min mice were 5 weeks old at the beginning of the study and received herbacetin for 15 weeks 5 days/week.

TABLE 1

| Group | Treatment | Amount of compound | No. of mice |
| --- | --- | --- | --- |
| 1 | Control | vehicle | 5 |
| 2 | herbacetin | 4 mg/kg B.W. | 5 |
| 3 | herbacetin | 2 mg/kg B.W. | 5 |
| Total | | | 15 |

Results of this study were very positive. Mice treated with 0.4, or 2 mg/kg BW of herbacetin exhibited smaller and fewer colon tumors. Herbacetin had no effect on body weight of APCMin+mice, suggesting that it was not toxic. Herbacetin prevents TPA-induced skin cancer carcinogenesis in SKH-1 hairless mice. Mice treated with herbacetin developed fewer papillomas (dose-dependent) compared to untreated control mice. Fewer mice developed papillomas when treated with herbacetin compared to untreated control mice. In addition, mice treated with herbacetin developed significantly smaller tumors compared to untreated controls.

Example 3

Athymic nude mice were inoculated in the right flank with HCT116 cells. Tumors were allowed to grow to an average of 40 mm$^3$ and then mice were divided into four equal groups with the same average tumor volume (FIG. 10). Treatment was initiated on Day 8 and continued to Day 20. The asterisk (*) indicates that the tumors from the vehicle-treated group were significantly large in volume than any of the three treated groups. No difference between treatment with 0.4 mg/kg B.W. herbacetin, 2 mg/kg B.W herbacetin or 200 mg/kg DFMO was observed. This result suggests that herbacetin is a much more potent (based on concentration) therapeutic agent than DFMO.

What is claimed is:

1. A method for inactivating ornithine decarboxylase (ODC) in a cell comprising contacting the cell in vitro or in vivo with an effective amount of 3,5,7,8,4'-Pentahydroxyflavone, or a pharmaceutically acceptable salt thereof.

2. A method for inhibiting cancer cell growth comprising contacting the cell in vitro or in vivo with an effective amount of 3,5,7,8,4'-Pentahydroxyflavone, or a pharmaceutically acceptable salt thereof.

3. A method for treating cancer in a mammal comprising administering to the mammal an effective amount of 3,5,7,8,4'-Pentahydroxyflavone, or a pharmaceutically acceptable salt thereof.

4. The method of claim 3, wherein the mammal is in need of such treatment.

5. The method of claim 3, wherein the mammal is diagnosed with cancer.

6. The method of claim 3, wherein the mammal is a human.

7. The method of claim 3, wherein the cancer is colon cancer or skin cancer.

8. A dermal product comprising 3,5,7,8,4'-Pentahydroxyflavone, or a pharmaceutically acceptable salt thereof, wherein the product prophylactically or therapeutically treats sunburn or other sun exposure and/or skin cancer in a mammal.

9. The product of claim 8, wherein the product is a sunscreen.

* * * * *